(12) United States Patent
Stathopoulos

(10) Patent No.: US 8,105,582 B2
(45) Date of Patent: Jan. 31, 2012

(54) TUMOUR VACCINE COMPRISING ALLOGENIC OR XENOGENEIC TUMOUR CELLS

(76) Inventor: Apostolos Stathopoulos, Luxembourg (BE)

( * ) Notice: Subject to any disclaimer, the term of this patent is extended or adjusted under 35 U.S.C. 154(b) by 182 days.

(21) Appl. No.: 12/161,418

(22) PCT Filed: Jan. 26, 2007

(86) PCT No.: PCT/EP2007/050807
§ 371 (c)(1),
(2), (4) Date: Aug. 18, 2009

(87) PCT Pub. No.: WO2007/085648
PCT Pub. Date: Aug. 2, 2007

(65) Prior Publication Data
US 2010/0055136 A1    Mar. 4, 2010

(30) Foreign Application Priority Data
Jan. 26, 2006    (GB) .................................. 0601598.6

(51) Int. Cl.
*A61K 39/00* (2006.01)
*A61K 35/12* (2006.01)
*A01N 63/02* (2006.01)
(52) U.S. Cl. ...................... 424/93.7; 424/277.1; 424/573
(58) Field of Classification Search ........................ None
See application file for complete search history.

(56) References Cited

FOREIGN PATENT DOCUMENTS
WO    WO 90/03183 A1    4/1990
WO    WO 00/33870 A2    6/2000
WO    WO 2004/018659 A1    3/2004

OTHER PUBLICATIONS

Rieger et al (Glossary of Genetics and Cytogenetics, 1976, pp. 289-290, definition for "inbred line").*
Abstract of Wheeler (Salud p'ublica de M'exico, (Jul.-Aug. 1997) 39 (4) 283-7).*
Blakeslee, J. R. et al., "Tumor Rejection and Immunotherapy Studies with Simian Virus 40-Induced Tumors," *Journal of Medicine*, 1973, pp. 233-247, vol. 4, No. 4, XP008077620.
Chan, A. D. et al., "Active Immunotherapy With Allogeneic Tumor Cell Vaccines: Present Status," *Seminars in Oncology*, Dec. 1998, pp. 611-622, vol. 25, No. 6, XP008077525.
Disis, M. L. et al., "Cancer Vaccines for the Treatment and Prevention of Non-Small-Cell Lung Cancer," *Clinical Lung Cancer*, May 2000, pp. 294-301, vol. 1, No. 4, XP008077643.
Dols, A. et al., "Allogeneic Breast Cancer Cell Vaccines," *Clinical Breast Cancer Supplement*, Feb. 2003, pp. S173-S180, vol. 3, Supplement 4, XP009064465.
Jiang, X. P. et al., "Vaccination with a Mixed Vaccine of Autogenous and Allogeneic Breast Cancer Cells and Tumor Associated Antigens CA15-3, CEA and CA125—Results in Immune and Clinical Responses in Breast Cancer Patients," *Cancer Biotherapy and Radiopharmaceuticals*, Nov. 5, 2000, pp. 495-505, vol. 15, No. 5, XP009064457.
Perlin, E. et al., "Carcinoma of the Lung: Immunotherapy with Intradermal BCG* and Allogeneic Tumor Cells," *International Journal of Radiation Oncology Biology Physics*, 1980, pp. 1033-1039, vol. 6.
Bystryn et al. "Double-blind trial of a polyvalent, shed-antigen, melanoma vaccine" *Clinical Cancer Research*, 2001, pp. 1882-1887, vol. 7, No. 7.
Henderson et al. "Cancer vaccines and immunotherapies; emerging perspectives" *Vaccine*, 2005, pp. 2359-2362, vol. 23, No. 17-18.
Hrouda et al. "Allogeneic whole-tumour cell vaccination in the rat model of prostate cancer" *BJU International*, 2000, pp. 742-748, vol. 86, No. 6.
Knight et al. "Allogeneic murine melanoma cell vaccine: A model for the development of human allogeneic cancer vaccine" *Melanoma Research*, 1996, pp. 299-306, vol. 6, No. 4.
Sosman et al. "Adjuvant immunotherapy of resected, intermediate-thickness, node-negative melanoma with an allogeneic tumor vaccine: impact of HLA class I antigen expression on outcome" *Journal of Clinical Oncology*, 2002, pp. 2067-2075, vol. 20, No. 8.
Souberbielle et al. "Comparison of four strategies for tomour vaccination in the B16-F10 melanoma model" *Gene Therapy*, 1998, pp. 1447-1454, vol. 5, No. 11.
Todryk et al. "Efficacy of cytokine gene transfection may differ from autologous and allogeneic tumour cell vaccines" *Immunology*, 2001, pp. 190-198, vol. 102, No. 2.
Vaishampayan et al. "Active immunotherapy of metastatic melanoma with allogeneic melanoma lysates and interferon α" *Clinical Cancer Research*, 2002, pp. 3696-3701, vol. 8, No. 12.
Yoshikawa et al. "Vaccine efficacy of fusogenic liposomes containing tumor cell-lysate against murine B16BL6 melanoma" *Biol. Pharm. Bull.*, 2006, pp. 100-104, vol. 29, No. 1.

* cited by examiner

*Primary Examiner* — Karen Canella
(74) *Attorney, Agent, or Firm* — Saliwanchik, Lloyd & Eisenschenk

(57) ABSTRACT

The present invention provides a composition for the treatment of a tumor, comprising: (i) allogeneic or xenogeneic tumor cells; and (ii) a pharmaceutically acceptable excipient. If two or more heterozygous individuals have the same cancer/tumor of the same or similar histological grade, then transplantation of tumor/cancer tissue/cells from one individual to another will not only induce rejection of the transplanted tissue/cancer, but will also increase the immunological awareness of the immune system to peptides shared between the tumors/cancers and other tumors possessing similar peptides.

13 Claims, 9 Drawing Sheets

TUMOUR VACCINE COMPRISING ALLOGENIC OR XENOGENEIC TUMOUR CELLS

This application is a National Stage Application of International Application Number PCT/EP2007/050807, filed Jan. 26, 2007; which claims priority to Great Britain Application No. 0601598.6, filed Jan. 26, 2006, which are incorporated herein in their entirety.

FIELD OF THE INVENTION

This invention relates to the treatment of tumours. In particular, this invention relates to the immune-mediated treatment of tumours.

BACKGROUND OF THE INVENTION

The immune system consists of two branches, that while separated by speed and specificity, are intricately linked, creating a rapid and directed response against both endogenous and exogenous insults[16,21]. The innate immune system provides immediate host defense against physical, chemical and microbiological insults[16,21]. It involves neutrophils, monocytes, macrophages, complement, cytokines and acute phase proteins[16,21]. Despite the lack of antigen specificity, the innate immune system is able to recognize self from non-self, foreign peptides[16,21]. Adaptive immunity, however, involves B- and T-lymphocytes in a highly specific antigen directed response[16,21]. One advantage of adaptive immunity is the potential for immune memory, leading to stronger and more rapid response on further stimulation[8,9].

The defining feature of adaptive immunity (specific immunity) is the use of T and B-lymphocytes bearing antigen-specific receptors in a targeted immune response[16,21]. The major T-cell effectors are the T-helper cells, bearing CD4 receptors and cytotoxic T-cells bearing CD8 receptors[16,21]. T-helper cells interact with MHC II, and are responsible for coordinating the immune response, recognizing foreign antigens, activating various parts of the immune system and activating B-cells. Cytotoxic T-cells interact with MHC I receptors and play a role in mounting an immune response against exogenous pathogens[16,21].

The Major Histocompatibility Complex (MHC) is a genetic region that codes for proteins that play an essential role in regulating and modulating immune response[10,16]. The gene products of the MHC are divided into two separate groups, based on structure and biological properties: MHC II and MHC II[10,16]. MHC class I receptors are present on all nucleated cells[10,16]. They present endogenously-synthesized peptides and are intimately involved in self-self recognition. MHC class II receptors are only found on cells involved with immune responses and present exogenously-derived proteins such as those from bacterial production[10,16]. Classically, MHC I was thought to be involved in tumour rejection, but more recently MHC II has been found to play a role.

The diversity of antigen binding by MHC class I molecules is based on three basic and interrelated principles. First, class I molecules have the ability to bind peptides with many different sequences[2,16]. These MHC class 1: antigen complexes can be recognized by the cytotoxic T-lymphocytes (CDS), eventually leading to the destruction of any cell carrying a similar foreign protein[2,16]. Secondly, each organism expresses a number of different class I genes[2,16]. Lastly, MHC exhibits polymorphisms with a number of alleles at each locus[2,16,23]. In humans, the MHC I is represented at more than one locus called the Human Leukocyte Antigen (HLA), the loci being HLA-A,-B and -C, the most polymorphic of which is HLA-B[16,23]. These factors imply a high degree of individual specificity and the need for a regulator to exert selective pressure: the cellular immune system.

It is this high degree of specificity and overriding selective pressure that is exploited in the transplantation of organs and tissues between individuals[23]. Identical twins and genetically close family members are less likely to reject transplanted tissue since they have similar HLA loci[16]. This is based on the fact that the MHC I are expressed co-dominantly and in most cases inherited intact without recombination[16,23]. Therefore, homozygous individuals such as identical twins and syngeneic rats could theoretically accept a brain tumour from his/her homozygous donor. Yet more critically, they would reject a brain tumour from a heterozygous donor based on a specific and targeted immune response.

As stated earlier, MHC class I receptors are surface glycoproteins located on most cells that play a crucial role in immune response, These MHC class I bind to antigenic peptides and interact with NK cells and CD8[5,16,25]. These peptides are derived from degraded endogenous proteins from virus and tumour infected cells[5,16,25]. Antigen processing is a complex mechanism that involves numerous steps. A defect in any of these steps may lead to non-expression of the MHC class I: antigen complex, and escape from T-cell recognition and destruction[12]. The loss of or dysregulation on MHC I complexes is a frequent mechanism for evading destruction from CD8[12]. Intuitively, one might assume that this "missing self"[17] marker might lead to increased recognition by NK cells, which are inhibited by interacting with the MHC I complex, and stimulated by cells with down-regulated HLA-2/HA expression[18]. Yet even with a fully functioning immune system, it is possible for tumours to evade recognition through the use of an elusive escape strategy[12]. Although the mechanism of escape is poorly understood, experiments have described several mechanisms allowing tumours to escape recognition by the immune system. These mechanisms range from loss or mutation of HLA halotypes to unresponsiveness to interferons[12]. So while a change of or loss of MHC class I receptors is associated with the genesis of various tumours, the presence of MHC class I molecules has been shown to participate in cancer resistance.

An example of the anti-tumourogenic effects of MHC class I molecule is in the immune surveillance of mitochondrial DNA integrity. In one study, one of the roles of MHC I molecules was to eliminate cells carrying mitochondrial mutation[13]. Human glioma cells carry multiple mutations in both the mitochondrial DNA and in the mitochondrial complex[7]. From this data, it is possible to assume that gliomas of the same histological type/grade will carry similar mutations in their DNA and have similar abnormal surface proteins associated with both MHC class I molecules and the cell membrane. Conversely, an intact immune system can also allow for the development and progression of tumours.

It has been shown that the progression of certain cancers is associated with the expression of tumour-specific antigens and an associated immune response[15]. Therefore, effective tumour rejection and immunity cannot be achieved solely by self-vaccination. Despite these barriers, there is increasing evidence that the immune system can be used to combat cancer. While both a dysregulated and normally functioning immune system fight against immune rejection of cancer, there have been reported results of the spontaneous rejection of malignant tumoure[19,26]. Interestingly, it has also been suggested that autoimmune diseases may contribute to a better prognosis in patients with malignant tumours[6,19]. In these patients, the majority of the IgG specificities identified share considerable homology with both human and microbial peptides[14]. This has lead to the hypothesis that molecular mimicry may initiate the observed tumour autoimmunity. Studies related to this have shown long term remission of malignant brain tumours after intracranial infection in four patients[4], and improved survival of cancer patients with microbial infection[20,22]. This brings into question whether the molecular mimicry induced autoimmunity can be used to treat tumours. Importantly, significant homology has been shown to exist between human proteins and proteins from other species[24]. Further experiments have shown that xenogeneic antigen from endothelial cells can break immune tolerance against autologous angiogeneic endothelial cells[20]. This suggests that self-tolerance to tumours may be broken through cross-reactivity with a homologous foreign antigen

SUMMARY OF THE INVENTION

The present invention is based on the realisation that, if two or more heterozygous individuals have the same cancer/tumour of a similar or same histological grade, then transplantation of tumour/cancer tissues/cells from one individual (or more) to another (or others) will not only induce rejection of the transplanted tissue/cancer, but will also increase the immunological awareness of the immune system to peptides shared between the tumours/cancers and other tumours possessing similar peptides. Allogeneic tumours may therefore be used to vaccinate an established tumour, reduce its size or eliminate it and establish lasting memory. This technique will not only lead to eventual rejection of the primary tumour, but will also lead to a lasting immunologic memory, preventing the organism from developing the tumour again.

According to a first aspect of the invention, a composition for the treatment or prevention of a tumour comprises
  (i) allogeneic or xenogeneic tumour cells; and
  (ii) a pharmaceutically acceptable excipient.

The allogeneic or xenogeneic cells may be provided from one or more allogeneic or syngeneic individuals and presented either as whole cells or as a lysate. The composition may also comprise a lysate of a syngeneic cell.

According to a second aspect of the invention there is the use of allogeneic or xenogeneic tumour cells in the manufacture of a medicament for the treatment of a tumour in a patient.

The medicament may further comprise a lysate of a syngeneic cell. The allogeneic or xenogeneic tumour cell may be a whole cell or may be a lysate.

The present invention not only treats tumours, but has the benefit that the immune system is able to effectively target the tumour, avoiding problems associated with delivery/targetting of conventional chemotherapeutics. In addition, chemotherapy has many undesirable side-effects, including baldness, nausea, diarrhea, anaemia and increased risk of infection, and these are avoided using the therapy of the invention.

DESCRIPTION OF THE DRAWINGS

The invention is described with reference to the accompanying figures, wherein.

DESCRIPTION OF THE INVENTION

Figure 1:
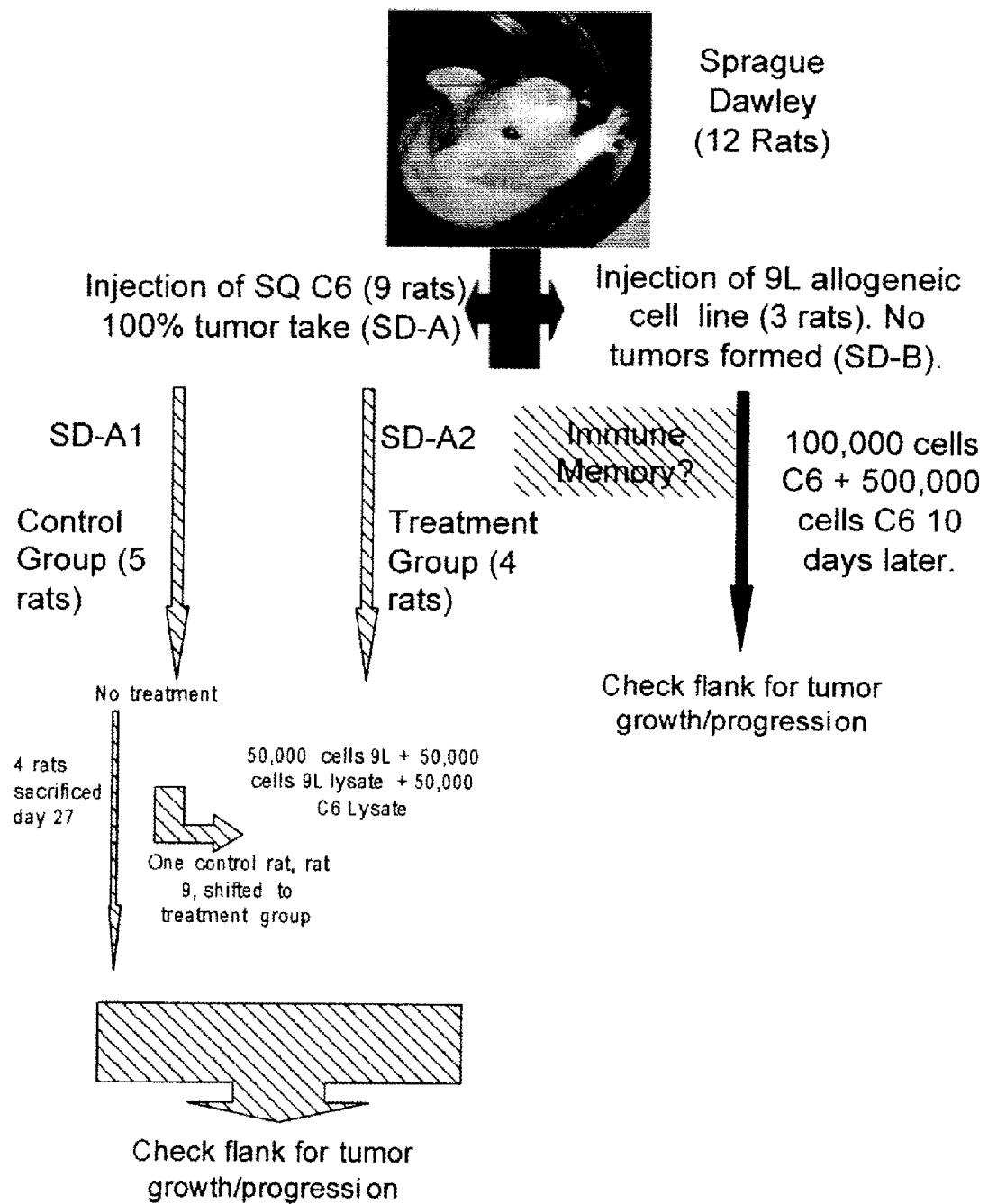
FIG. 1 is a schematic of experimental design in Sprague Dawley Rats. Rats were divided in two groups. Those receiving syngeneic cell line (C6; SD-A) and those receiving allogeneic cell line (9L; SD-B). The syngeneic arm of the study was divided into two groups: control (5 rats; SD-A1) and treatment (4 rats; SD-A2). On day 27, 4SD-A1 rats were sacrificed. At this time the remaining SD-A1 rat (Rat 9) entered the treatment protocol. All SD rats initially injected with the 9L allogeneic arm (SD-B) received flank injections with the syngeneic C6 cell line (100,000 cells), followed ten days later with an additional bolus of 500,000 C6 cells.

The present invention utilises allogeneic or xenogeneic tumour cells and syngeneic cells, to increase the awareness of a patient's immune system, to treat a tumour, The tumour cell vaccines of the present invention share similar peptides in the cancer/tumour with the same histological grade, with different MHC I molecules.

The vaccines are prepared with whole allogeneic or xenogeneic tumour cells. or lysates of allogeneic or xenogeneic tumour cells. The vaccine may further comprise a lysate of one or more syngeneic cells.

The allogeneic or xenogeneic cells will preferably be tumour cells of the same (or similar) histological grade as the tumour cells of the patient to be treated. Accordingly, if the patient has a brain glioblastoma, the vaccine will be prepared with allogeneic or xenogeneic brain glioblastoma cells. In this way, the peptides comprised in the cells will be similar and will increase the likelihood of the appropriate immune response being generated.

The vaccine compositions will usually comprise allogeneic or xenogeneic cells/lysates from two or more heterozygous individuals. Preferably, the vaccine compositions are prepared using allogeneic or xenogeneic cells/lysates from at least three heterozygous individuals.

The term "allogeneic" refers to cells taken from different individuals of the same species.

The term "xenogeneic" means that which is derived or obtained from an organism of a different species.

The term "syngeneic" refers to genetically identical members of the same species. For example identical twins will have cells and tissues that are syngeneic.

Reference is made in the description to cancers/tumours of the "same or similar histological grade". The skilled person will understand that this is refers to cancers of the same type and which exhibit the same level of differentiation. Grading may be carried out according to the Elston-Ellis method (Simpson et al, J. Clin. Oncol., 2000; 18:2059-2069).

The reference to "cancer" and "tumour" are used interchangeably.

The present invention provides a pharmaceutical composition comprising administering a therapeutically effective amount of allogeneic or xenogeneic tumour cells and optionally pharmaceutically acceptable excipients.

The pharmaceutical compositions may be for human or animal usage in human and veterinary medicine and will typically comprise a pharmaceutically acceptable excipient. Acceptable excipients for therapeutic use are well known in the pharmaceutical art, and are described, for example, in Remington's Pharmaceutical Sciences, Mack Publishing Co. (A. R. Gennaro edit. 1985). The choice of pharmaceutical excipient can be selected with regard to the intended route of administration and standard pharmaceutical practice. The pharmaceutical compositions may comprise as—or in addition to—the excipient any suitable binder(s), lubricant(s), suspending agent(s), coating agent(s), solubilising agent(s). The reference to "excipient" includes diluents and carriers.

Preservatives, stabilizers and dyes may be provided in the pharmaceutical composition. Examples of preservatives include sodium benzoate, sorbic acid and esters of p hydroxybenzoic acid. Antioxidants and suspending agents may be also used.

There may be different composition/formulation requirements dependent on the different delivery systems.

Where appropriate, the pharmaceutical compositions can be administered by injection, parenterally, for example intravenously, intramuscularly or subcutaneously. For parenteral administration, the compositions may be best used in the form of a sterile aqueous solution which may contain other substances, for example enough salts or monosaccharides to make the solution isotonic with blood.

Vaccines may be prepared from the compositions of the invention.

The preparation of vaccines which contain immunogenic cells as active ingredients, is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the cells encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP I9835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAB-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminum hydroxide), or a mixture of Amphigen and Alhydrogel are used. Only aluminum hydroxide is approved for human use.

The proportion of immunogen and adjuvant can be varied over a broad range so long as both are present in effective amounts. For example, aluminum hydroxide can be present in an amount of about 0.5% of the vaccine mixture (Al2O3 basis). Conveniently, the vaccines are formulated to contain a final concentration of immunogen in the range of from 0.2 to 200 mg/ml, preferably 5 to 50 mg/ml, most preferably 15 mg/ml.

The vaccines are conventionally administered parenterally, by injection, for example, either subcutaneously or intramuscularly.

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The amounts of each component will be apparent to the skilled person. Suitable amounts are as follows:
a) $1 \times 10^6$ ($\pm 0.5 \times 10^6$) allogeneic tumour cells with different MHC I modified by DNP.
b) $2 \times 10^6$ ($\pm 1 \times 10^6$) autologous tumour cells modified by DNP and irradiated.
c) $2 \times 10^6$ ($\pm 1 \times 10^6$) lysate cells of autologous (syngeneic) tumour.
d) $1 \times 10^6$ ($\pm 0.5 \times 10^6$) lysate cells of allogeneic tumour.

The invention will now be described further with reference to the accompanying figures.

EXAMPLE

Cell Lines and Cell Culture:

The cell lines used in this experiment were the rat glioma cell lines (9L, C6, RG2), and the human glioma cell lines (U87, LN229). All lines were obtained from the American Type Tissue Collection (ATTC), and grown in Dulbecco's Modified Eagles Medium (DMEM) (GIBCO, Grand Island, N.Y.) supplemented with 10% heat-killed Fetal Calf Serum (FCS). 5% penicillin-streptomycin, and Hepes buffer in a humidified incubator at 37° C. in a 5% $CO_2$ atmosphere.

Cell Lysate Preparation:

$1.0 \times 10^5$ cells were placed in 5 ml tube in culture medium and centrifuged for 5 min at $2.5 \times 10^3$ rpm. The supernatant was discarded and 150 µl of sterile distilled water was added to the tube. The cell/water solution was mixed well and transferred to a 1.0 ml Eppendorf tube and centrifuged at $1.0 \times 10^4$ for 10 minutes. The supernatant was not discarded and this entire solution was used for cell lysate injections.

Antibodies and Immunohistochemistry:

Tumour samples taken from the Fisher 344 rats were frozen in Optimum Temperature Compound (OTC) and cut into 7 µm sections on a cryostat. These sections were dried, fixed with acetone, and washed well with PBS for 1-2 minutes. Blocking was done using the immune serum from the species the secondary antibody was taken from. Slides were washed thoroughly again and then stained with primary antibody against CD-4, CD-57 (Nora Castro Lab Ltd., Burlingame, Calif.). CD-8, dendritic reticulum cells (DRC) (Dako Corporation, Carpenteria, Calif.), CD-20, CD-68 (Ventana, Tucson, Ariz.). Slides were washed again and a secondary biotinylated antibody was added. They were rinsed again and placed in a solution of 3% hydrogen peroxidase and 9 parts 1% sodium azide in PBS. Slides were then rinsed and ABC was added for 30-40 minutes. They were washed with PBS and developed using diaminobezidine tetrahydrochloride and counterstained. Photos of all slides were taken by light microscopy.

Tumour Growth Analysis:

All tumours were found through visual inspection and palpation. Once discovered, the area around the tumour was further exposed by shaving with an electric razor. At the time of injection, tumour size was measured in millimeters using Vernier calipers. Measurements were taken in the cranial/caudal (length), superior/inferior (height), and medial/lateral (width) direction. Tumour volume was calculated by length×width×height×0.5.

In-vivo Studies:

All animal protocols were approved by the Institutional Animal Care and Use Committee (IACUC) of the University of Southern California. All rats were maintained in a pathogen free environment. For the experiment, we used Sprague Dawley and Fisher 344 rats. All rats were male and between the ages of 4-6 weeks. Rats were obtained from Harlan (Indianapolis, Ind.). In the subcutaneous tumour model, C6 and 9L were collected using only DMEM to wash them from the tissue culture flasks. Syringes were then prepared containing 100,000-150,000 cells suspended in 150 µl.

Sprague Dawley (SD) rats were divided into two groups (FIG. 1). SD-A (9 rats) were implanted with the C6 glioma, a syngeneic like glioma cell line for SD rats. SD-B (3 rats) were injected with the 9L allogeneic cell line. Once a palpable flank tumour developed in the Group A rats, they were further divided into two groups. SD-A1 (control group-5 rats) received no injections. SD-A2 (treatment group-4 rats) were injected with a combination of allogeneic 9L cells, allogeneic 9L lysate, and syngeneic C6 lysate. On day 27, 4 of the 5 SD-A1 were sacrificed. At this time, one of the control rats, rat 9, started receiving the same treatment protocol as the SD-A2 rats. The combination of allogeneic cells, syngeneic and allogeneic lysates, was used to enhance the immune response. SD-B rats, which never formed tumours, were tested for immune memory by challenging them with syngeneic C6 cells (100,000 cells), and another boost of 500,000 C6 cells 10 days later, and checked for formation of a flank tumour.

Figure 2:
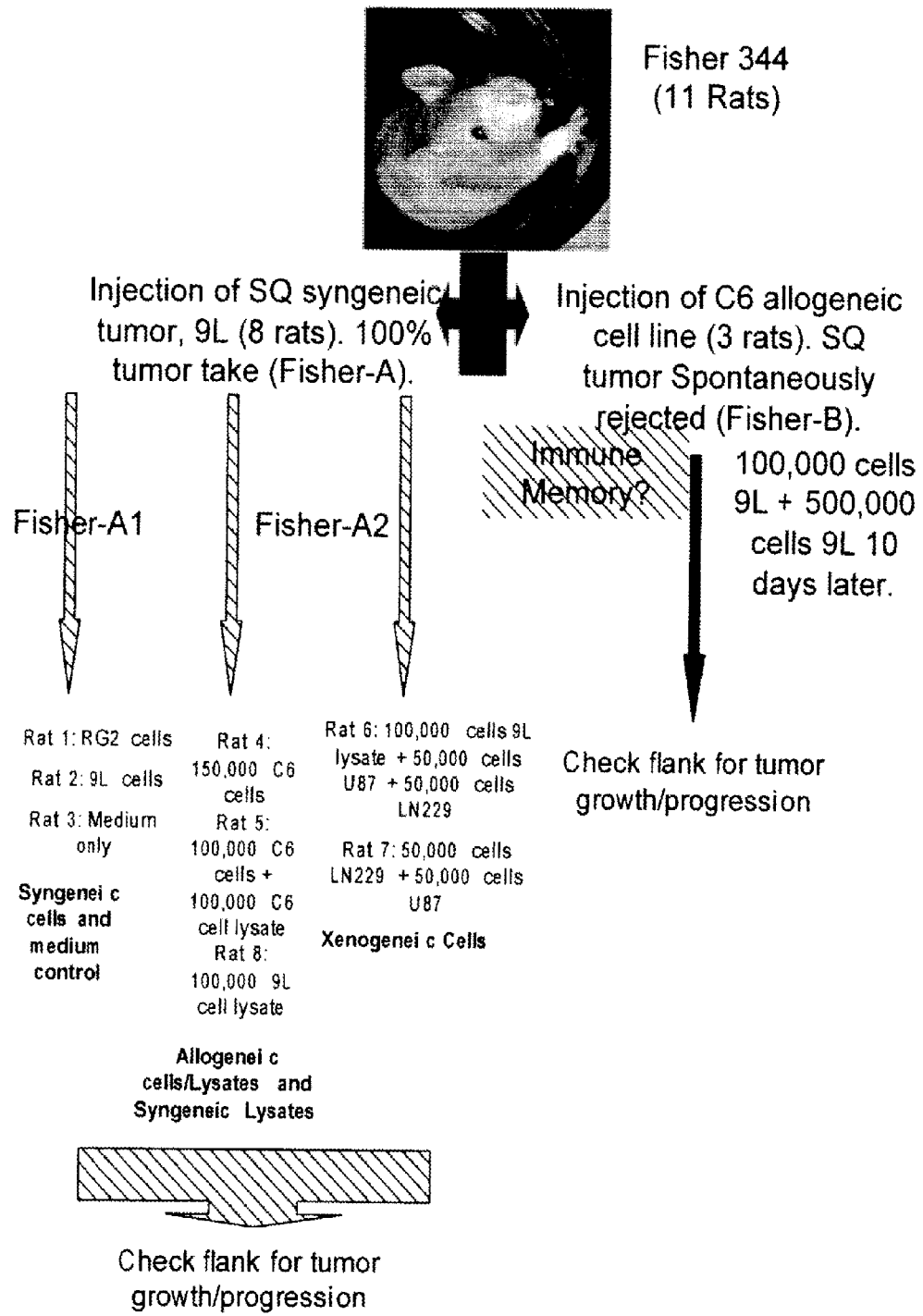
FIG. 2 is a schematic of experimental design in Fisher 344 rats. Rats were divided in two groups. Those receiving syngeneic 9L cell line (Fisher A) and those receiving allogeneic C6 cell line (Fisher B). The rats in the syngeneic group (Fisher A) were divided into a control group (Fisher A-1) and a treated group (Fisher A-2). Fisher A-1 rats were challenged with syngeneic RG2, 9L, or medium only. Fisher A-2 rats were treated with allogeneic cells, allogeneic cells and cell lysate, syngeneic cell lysate and xenogeneic cells, or xenogeneic cells alone. Fisher B rats were initially injected with C6 allogeneic cells. They were subsequently challenged with flank injections of syngeneic 9L cells (100,000 cells) followed ten days later with an additional bolus of 500,000 cells.

Fisher rats were also divided into two groups (FIG. 2). Fisher-A (8 rats) were implanted with the syngeneic 9L cell line. Fisher-B (3 rats) were injected with the allogeneic C6 cell line. Once a palpable flank tumour developed in the Fisher-A rats, they were further subdivided into two groups. Fisher A-1 (control group-3 rats) received injections of syngeneic 9L cells, syngeneic RG2 cells, or medium only. Fisher A-2 (treatment group-5 rats) received a combination of allogeneic C6 cells, allogeneic C6 cell lysate, or xenogeneic U87 and LN229 cells (see FIG. 2). Fisher B rats, which initially formed tumours that were subsequently rejected, were tested for immune memory by challenging them with a combination cocktail of syngeneic 9L cells and lysate, and checked for tumour growth.

Harvesting Subcutaneous Tissue:

All experimental animals were euthanized with an overdose of pentobarbital. All tumours were removed and dissected under sterile conditions, cut into 4 pieces and stored at −80° C. All tumour sections were cut at 7 µm and stained by immunohistochemistry.

Results

Most studies of glioblastoma employ small laboratory animal models. The immune-competent host models most frequently used include two different strains of rat, the Sprague Dawley and the Fisher 344 rats[1]. C6 is a syngeneic-like cell line for the SD rats, while the 9L and RG2 cell lines are syngeneic for the Fisher 344 rats[1,11].

Three of the Fisher rats were injected with C6 cell line (Fisher B). While well circumscribed tumours did form, they were subsequently rejected in forty days. A similar procedure was used to treat three SD rats with 9L cell line (SD-B). Each of the SD rats rejected the 9L tumour without visible or palpable tumour growth. The SD-A rats were each injected with the C6 cell line. All of these rats developed visible tumours within ten days. At this point, five rats were kept as a control group (SD-A1) while the remaining four rats were placed into treatment groups (SD-A2). On day 27 rats 1-4 were sacrificed and an attempt was made to "rescue" rat 9. At this time, rat 9 entered the treatment group and started receiving the same injections as the SD-A2 group.

Figure 3:
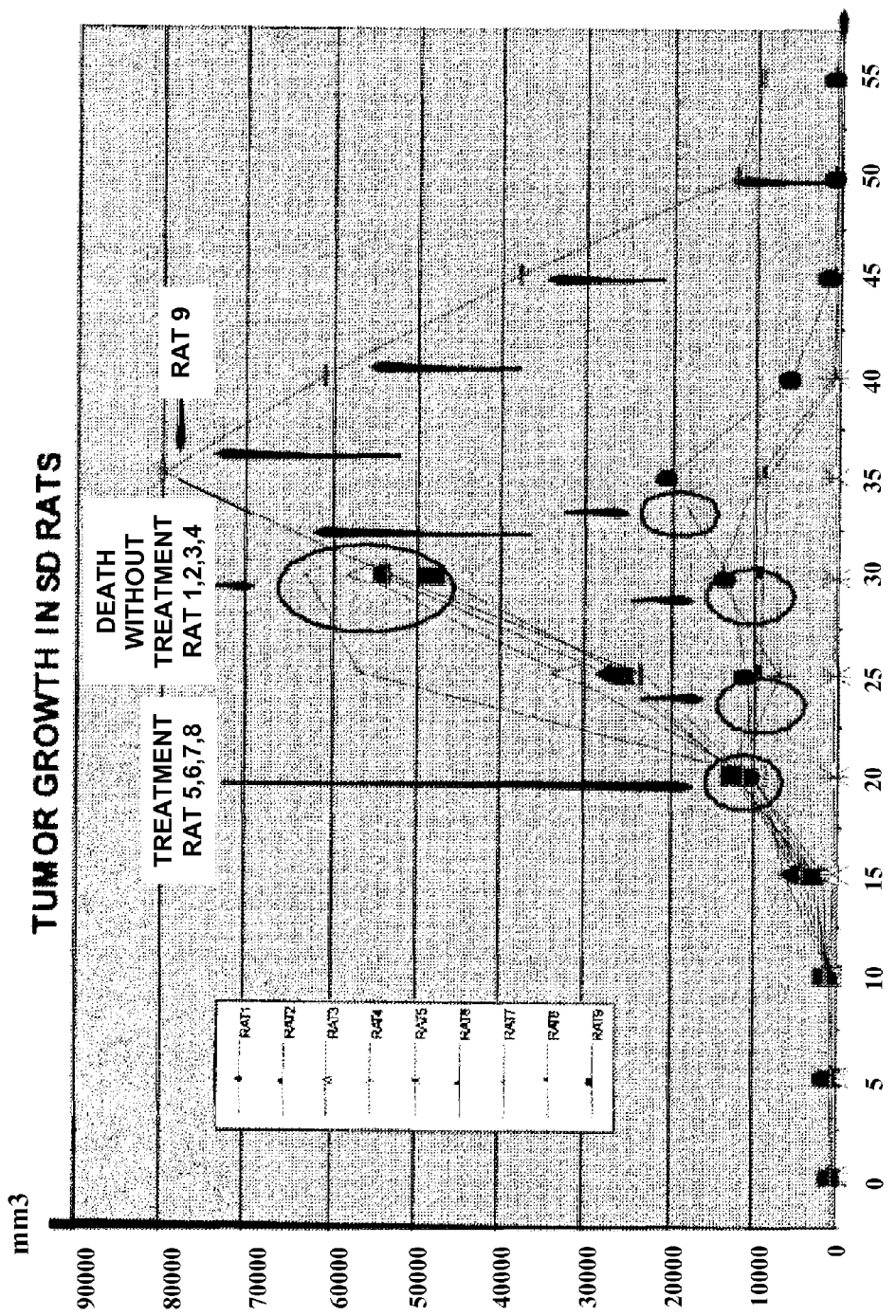
FIG. 3 is a graph charting tumour evolution/progression in 9 SD rats with subcutaneously implanted syngeneic tumour (C6). Rats were placed in either control or treatment groups as previously described. Tumour progression was determined through measurements of tumour volume (mm$^3$). Rat 1,2,3,4 received no treatment after C6 tumour implantation. Rat 5,6, 7,8 received treatment with allogeneic 9L cells and lysates with syngeneic C6 lysate. Rat 9 was allowed to form a very large tumour before it was switched to the treatment group as in Rats 5-8.

We analysed the tumour growth and treatment response in the nine SD-A rats (FIG. 3). In the treated SD-A2 rats (rats 5-8), individual rats were given different combinations of allogeneic and syngeneic lysates, as well as cells. For instance, after five days, rat number 5 had a palpable flank tumour and received one injection contralateral to the tumour with allogeneic 9L lysates (50,000), syngeneic C6 lysates (50,000), and 9L allogeneic cells (50,000). Five days after injection, the tumour resolved. Rats 6,7,8 (SD-A2 rats) all had visible tumours 18 days post injection. At this time, they each received an injection with 50,000 allogeneic 9L lysate cells plus 50,000 syngeneic C6 lysate cells and 50,000 9L allogeneic cells. These injections were repeated on days 23 and 28. Rat 6 had an additional treatment at day 33, 15 days after treatment began. The untreated rats (SD-A1, rats 1-4) were sacrificed 27 days post injection due to tumour size. Compared to the tumour progression in the untreated rats (rats 1-4), rats 5,6,7,8 (SD-A2) had complete resolution of tumours. Rat number nine began the experiment in the non-treated group, and then was rescued days after sacrificing rats 1-4. Rat 9 received injections every four days with allogeneic 9L lysates (50,000) plus C6 syngeneic lysates (50,000) and 9L allogeneic cells (50,000) and was sacrificed for histological analysis at day 55, when tumour size was 11% from the initial time of rescue.

Twenty days later, the "treated" SD rats with no measurable tumour were reinjected in the contralateral hind flank with the same syngeneic C6 tumour cell line that caused the original tumour, using 100,000 cells first and five times as many cells (500,000 cells) ten days after. The rats were monitored every three days for any sign of visual or palpable tumour growth. At 160 days, the SD rats remained tumour free.

Figure 4:
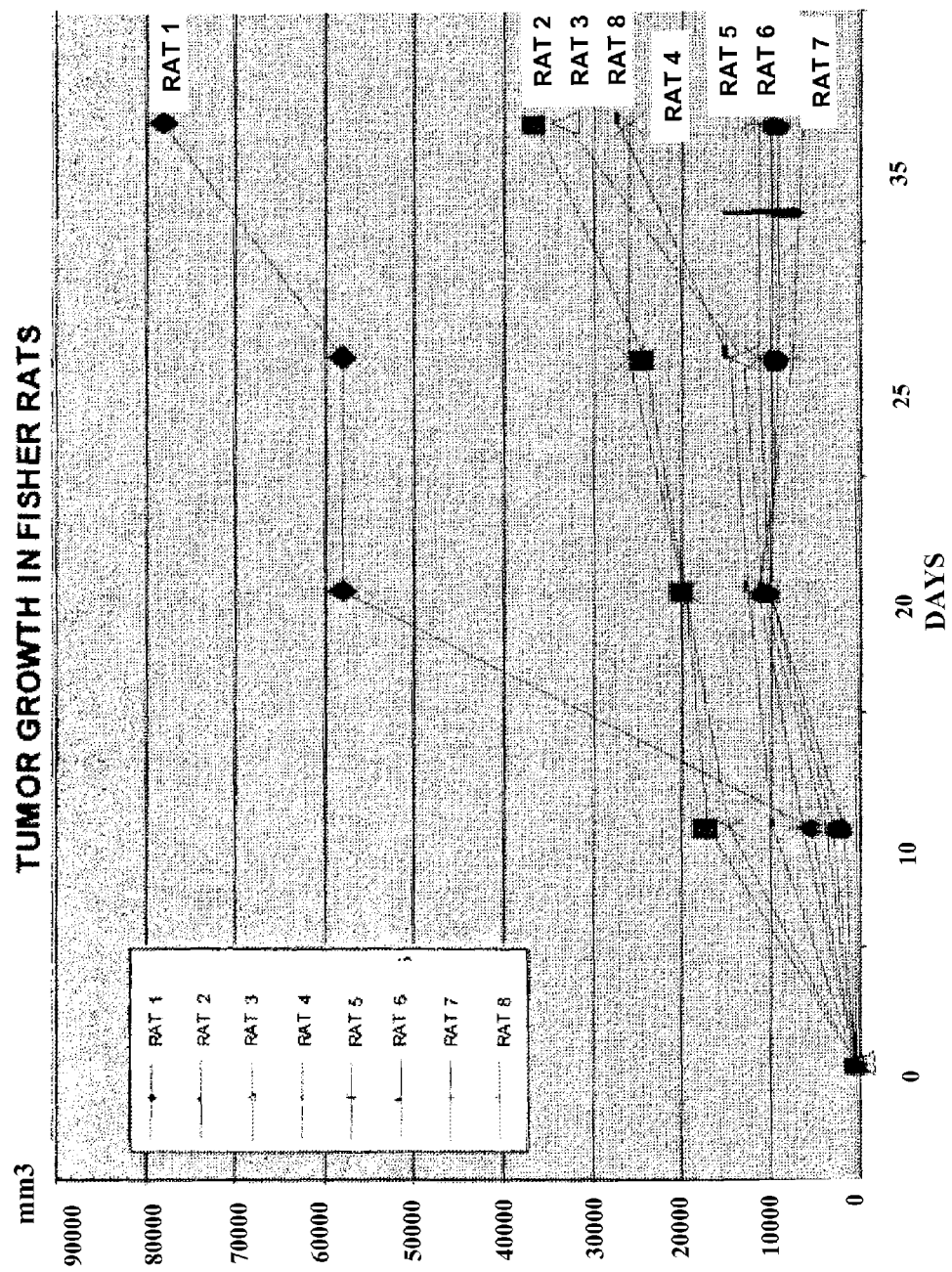
FIG. 4 is a graph charting tumour evolution/progression in Fisher 344 rats with subcutaneously implanted syngeneic tumour (9L). Control rats (Fisher A-1) were then injected with syngeneic RG2 cells (Rat 1), syngeneic 9L cells (Rat 2), or medium alone (Rat 3). Rat 1 had double the dosage of cells injected, and formed an extremely large tumour. Treated rats (Fisher A-2) were treated with allogeneic C6 cells alone (Rat 4), allogeneic C6 cells and lysate (Rat 5), syngeneic 9L lysate and xenogeneic U87 and LN229 cells (Rat 6), xenogeneic U87 and LN229 cells alone (Rat 7). Rat 8 was treated with syngeneic 9L cell lysate alone. Tumour progression was determined through measurements of tumour volume (mm$^3$).
Figure 5A:
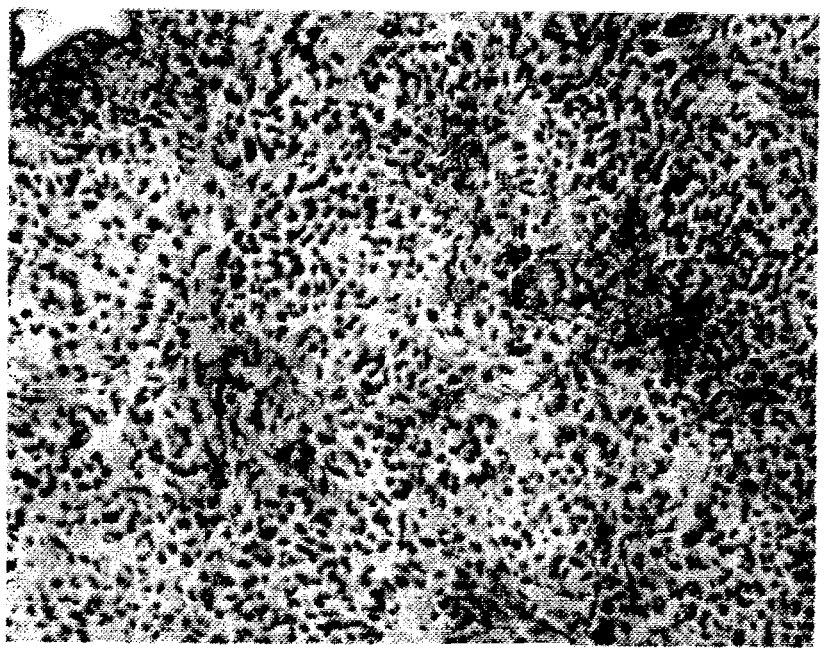
FIGS. 5A and 5B show tumour sections taken from FIG. 5A control and FIG. 5B treatment Fisher 344 rats. Sections were cut at a thickness of 7 μm and stained with an antibody directed against CD4 receptor according to the previously described protocol. Arrows indicate the location of cells staining positively for the CD4 surface marker. The magnification of both control FIG. 5A and treatment FIG. 5B sample is 40×.
Figure 5B:
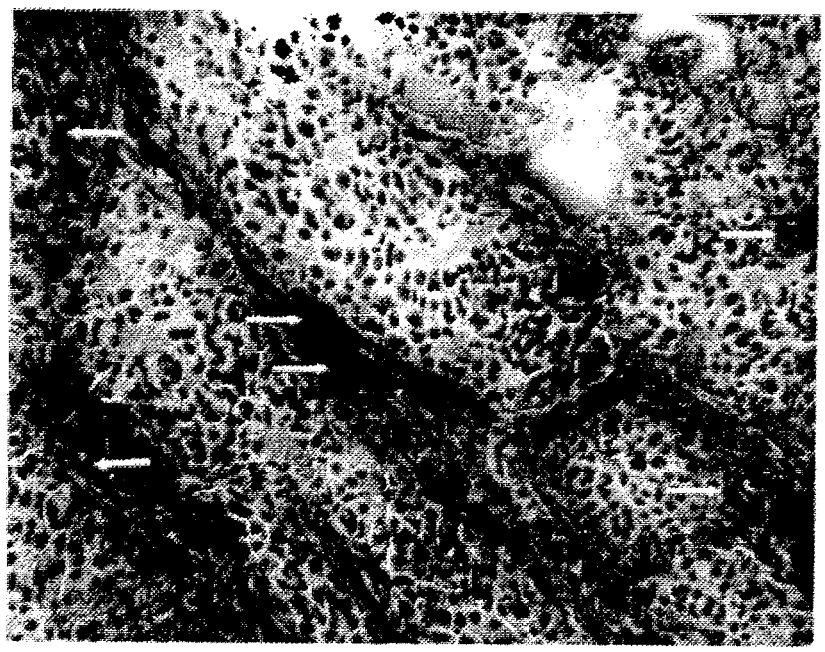
Figure 6A:
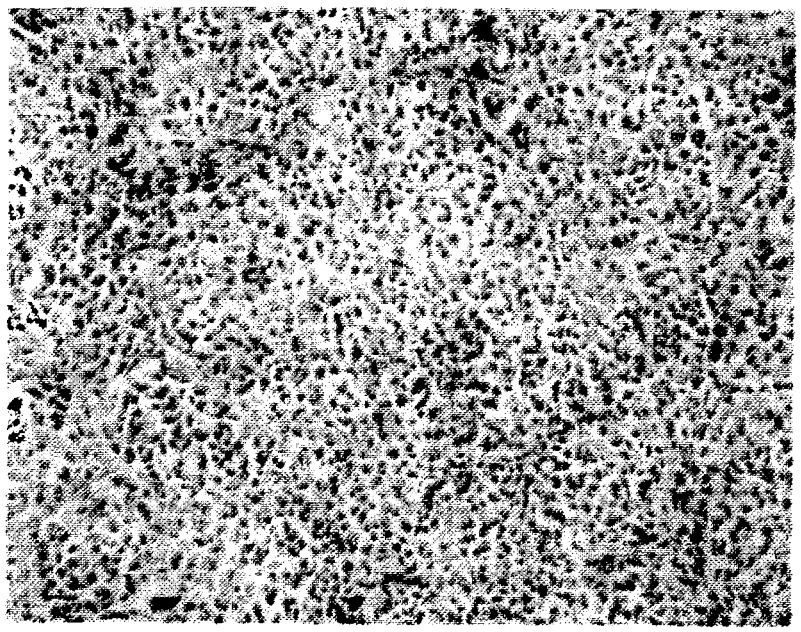
FIGS. 6A and 6B show tumour sections taken from FIG. 6A control and FIG. 6B treatment Fisher 344 rats. Sections were cut at a thickness of 7 μm and stained with an antibody directed against CD8 receptor according to the previously described protocol. Arrows indicate the location of cells staining positively for the CD8 surface marker. The magnification of both control FIG. 6A and treatment FIG. 6B sample is 40×.
Figure 6B:
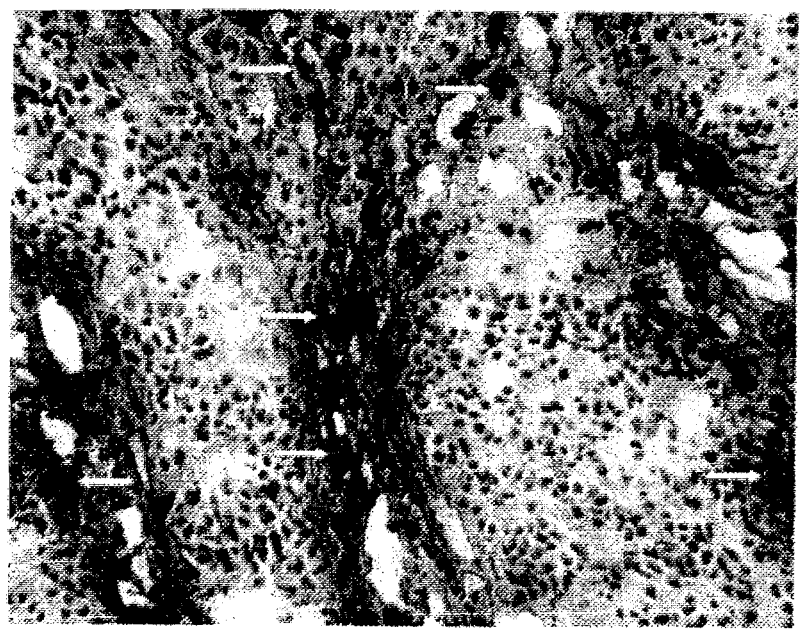
Figure 7A:
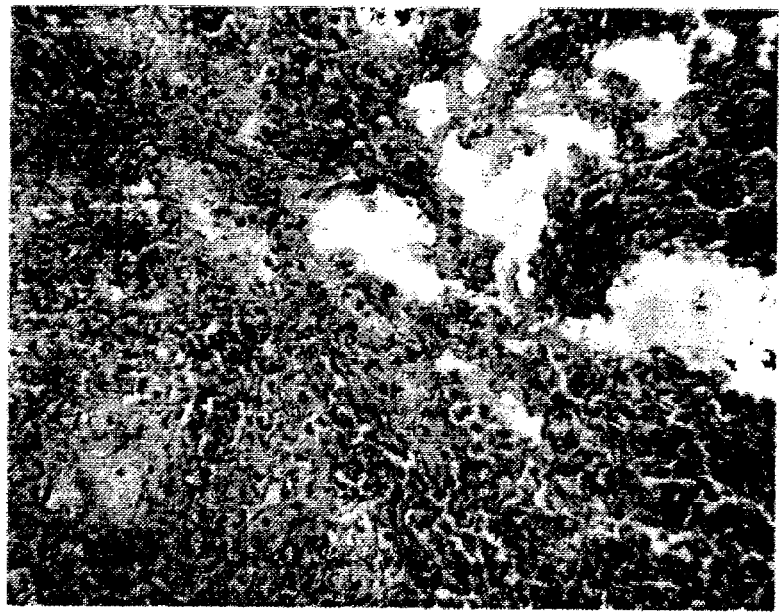
FIGS. 7A and 7B show tumour sections taken from FIG. 7A control and FIG. 7B treatment Fisher 344 rats. Sections were cut at a thickness of 7 μm and stained with an antibody directed against B-lymphocytes (CD 20) according to the previously described protocol. Arrows indicate the location of cells staining positively for the CD 20 surface marker (FIG. 5B). The magnification of both control FIG. 7A and treatment FIG. 7B sample is 40×.
Figure 7B:
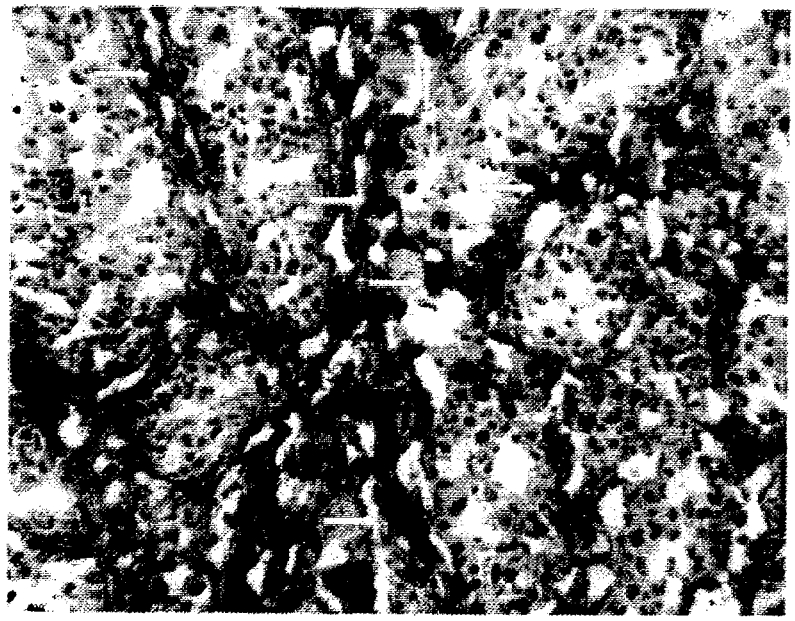
Figure 8A:
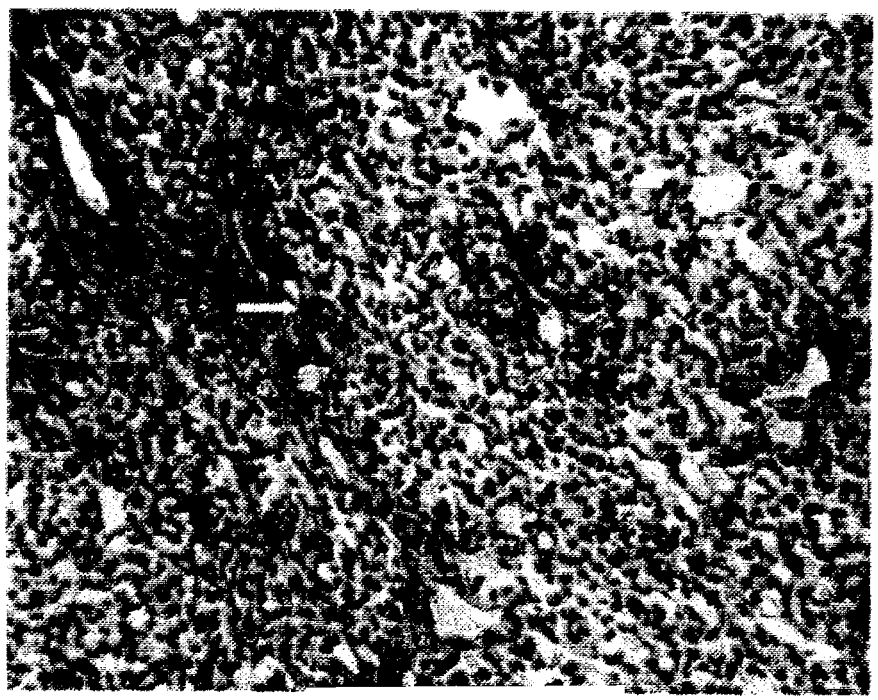
FIGS. 8A and 8B show tumour sections taken from FIG. 8A control and FIG. 8B treatment Fisher 344 rats. Sections were cut at a thickness of 7 μm and stained with an antibody directed against macrophages (CD 68) according to the previously described protocol. Arrows indicate the location of cells staining positively for the CD 68 surface marker. The magnification of both control FIG. 8A and treatment FIG. 8B sample is 40×.
Figure 8B:
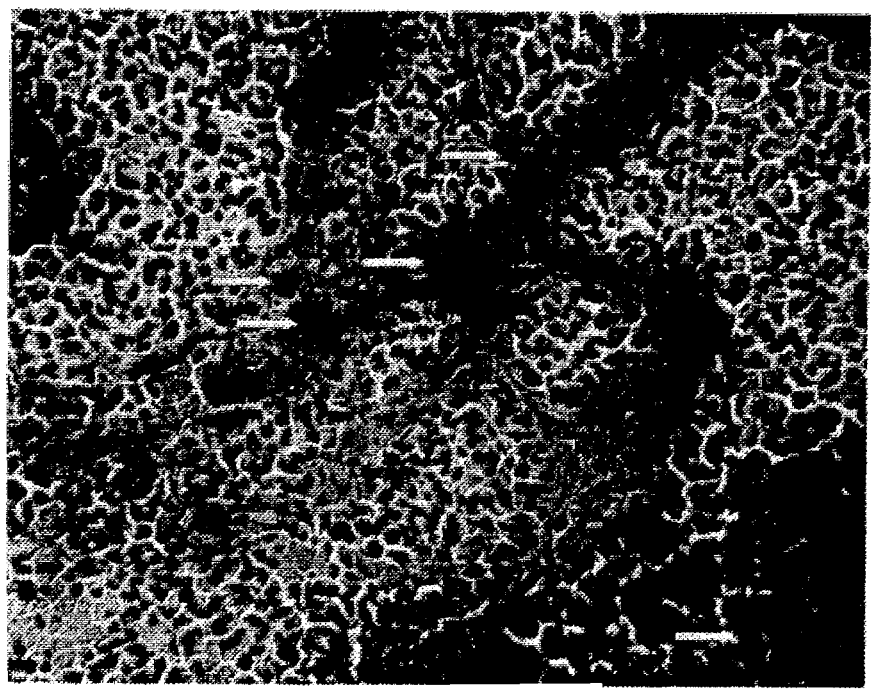
Figure 9A:
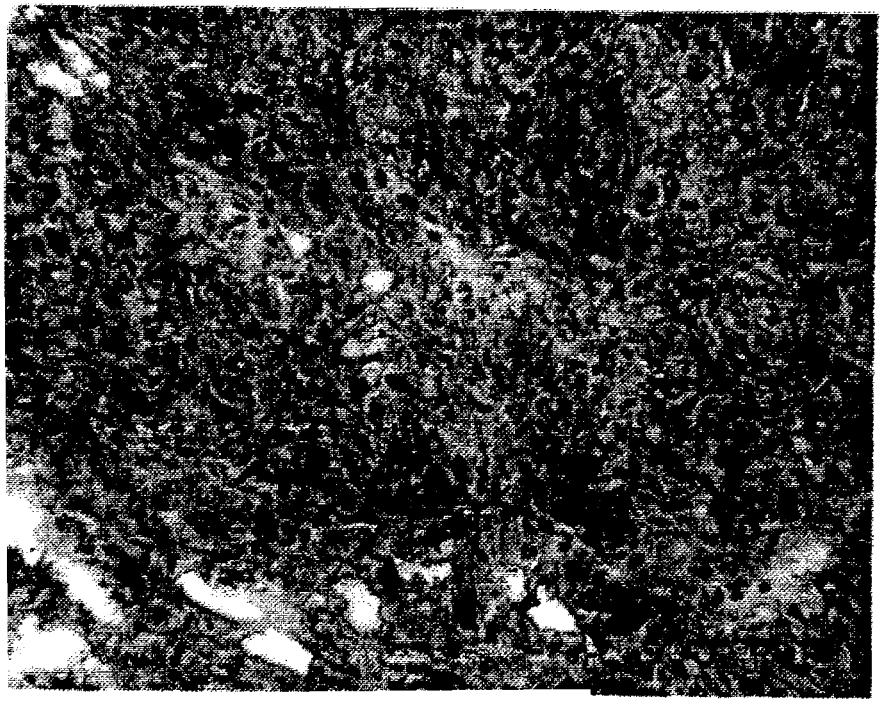
FIGS. 9A and 9B tumour sections taken from FIG. 9A control and 9B treatment Fisher 344 rats. Sections were cut at a thickness of 7 μm and stained with an antibody directed against Dendritic cell marker (DRC) according to the previously described protocol. Arrows indicate the location of cells staining positively for the DRC surface marker. The magnification of both control FIG. 9A and treatment FIG. 9B sample is 40×.
Figure 9B:
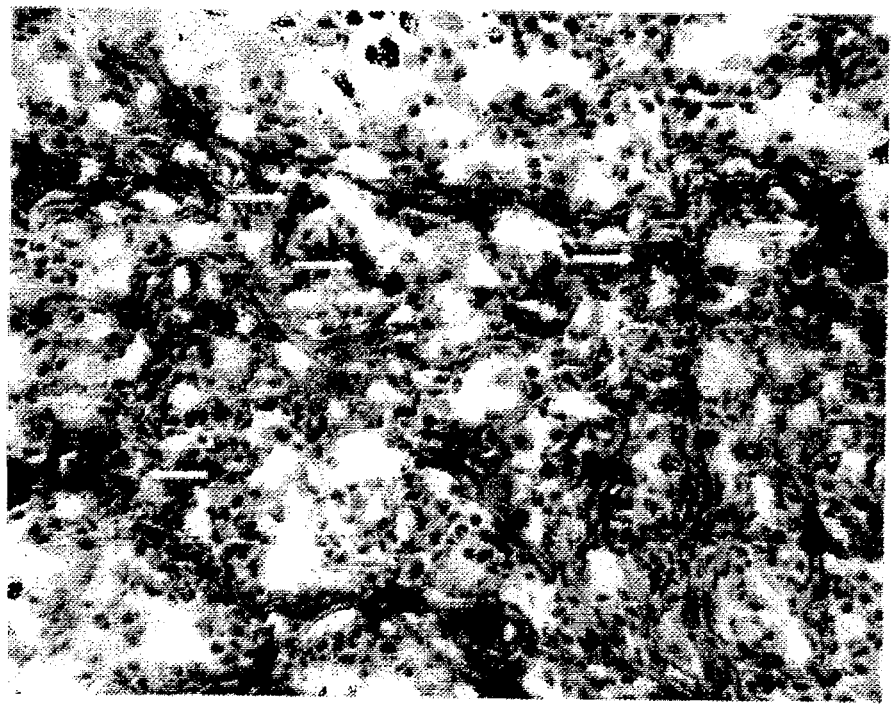

FIG. 4 shows tumour growth and response to the treatment of eight Fisher rats (Fisher-A) implanted with 9L cells. Rats 1, 2 and 3 (Fisher A-1) received contralateral flank injections at day 20 with syngeneic RG2 (100,000 cells; rat 1) and 9L (100,000 cells; rat 2), or medium alone (rat 3). There was no decrease in tumour size, and the RG2 even seemed to have a synergistic effect in rat 1. Rats 4-8 (Fisher A-2), injected with C6 allogeneic cells/C6 allogeneic lysate, 9L syngeneic lysate, or U87 and LN229 xenogeneic cells, all appeared to have a reduction in tumour size.

All Fisher 344 rats were sacrificed at day 40 when they developed a foot drop and inability to ambulate. The tumours from each of these rats was removed and cut for staining. We found our treatment tumours to have significantly greater numbers of CD4, CD8, B-lymphocyte (CD20), macrophage (CD68), and dendritic cells than the control tumours (FIGS. 3-7).

To determine the role of immune memory, we examined whether the SD and Fisher 344 rats initially injected with an allogeneic cell line would be able to accept a syngeneic cell line. The Fisher 344 rats who rejected the C6 (Fisher B) after 40 days were re-injected with syngeneic 9L cells; the SD rats (SD-B) who initially rejected the 9L cell line were injected with C6 cells. All injections were done in the contralateral flank to the original injection and with 500,000 cells. In the SD rat, no visual or palpable tumour developed. In the Fisher, a small (<1 cm×<1 cm×1 cm) growth developed at the injection site. This growth was noticeable only to palpation, and became progressively smaller and completely undetectable by 10 days. Both strains of rat remained without tumour at 150 days.

These results suggest that the repeated subcutaneous injection of allogeneic (or xenogeneic) cells, allogeneic cell lysates and syngeneic cell lysates lead to the reduction in tumour size by increasing the immunological awareness.

All publications referred to in the description are incorporated herein by reference.

REFERENCES

1. Beutler A S, Banck M S. Wedekind a et al: Tumour gene therapy made easy: allogeneic major histocompatibility complex in the C6 rat glioma model. Hum Gene Ther 10:95-101. 1999
2. Bjorkman P J, Saper M A, Samraoui B, et al: Structure of the human class I histocompatibility antigen, HLA-A2. Nature 329:506-512, 1987
3. Boudreau C R, Yang I, Liau L M: Gliomas: advances in molecular analysis and characterization. Surg Neurol 64:286-294; discussion 294. 2005
4. Bowles A P. Jr., Perkins F: Long-term remission of malignant brain tumours after intracranial infection: a report of four cases. Neurosurgery 44:636-642: discussion 642-633. 1999
5. Budd R C: Activation-induced cell death. Curr Opin Immunol 13:356-362, 2001
6. Bystryn J C, Rigel D, Friedman R J, et al: Prognostic significance of hypopigmentation in malignant melanoma. Arch Dermatol 123:1053-1055, 1987
7. DeHaan C, Habibi-Nazhad B, Yan F, et al: Mutation in mitochondrial complex I ND6 subunit is associated with defective response to hypoxia in human glioma cells. Mol Cancer 3:19, 2004
8. Delves P J, Roitt I M: The immune system. First of two parts. N Engl J Med 343:37-49, 2000
9. Delves P J, Roitt I M: The immune system. Second of two parts. N Engl J Med 343:108-117, 2000
10. Duquesnoy Ri, Trucco M: Genetic basis of cell surface polymorphisms encoded by the major histocompatibility complex in humans. CS Rev Immunol 8:103-145, 1988
11. Ehtesham M. Kabos P. Gutierrez M A, et al: Intratumoural dendritic cell vaccination elicits potent tumouricidal immunity against malignant glioma in rats. J Immunother 26:107-116, 2003
12. Garcia-Lora A, Algarra 1, Garrido F: MHC class I antigens, immune surveillance, and tumour immune escape. J Cell Physiol 195:346-355, 2003
13. Gu Y, Wang C, Roifman C M, et al: Role of MHC class I in immune surveillance of mitochondrial DNA integrity. J Immunol 170:3603-3607, 2003
14. Hansen M H, Ostenstad B, Sioud M: Antigen-specific IgG antibodies in stage IV long-time survival breast cancer patients. Mol Med 7:230-239, 2001
15. Jager D. Jager F, Knuth A: Immune responses to tumour antigens: implications for antigen specific immunotherapy of cancer. J Clin Pathol 54:669-674, 2001
16. Janeway C, National Center for Biotechnology Information (U.S.): Immunobiology S the immune system in health and disease, ed 5th. New York: Garland Pub. 2001
17. Ljunggren H G, Karre K: In search of the missing self: MHC molecules and NK cell recognition. Immunol Today 11:237-244. 1990
18. Moretta A, Bottino C, Vitale M, et al: Receptors for HLA class-I molecules in human natural killer cells. Annu Rev Immunol 14:619-648, 1996

19. Palo J, Duchesne J. Wikstrom J: Malignant diseases among patients with multiple sclerosis. J Neurol 216:217-222, 1977
20. Papachristou D N, Fortner J G: Effect of postoperative wound infection on the course of stage II melanoma. Cancer 43:1106-1111, 1979
21. Parkin J, Cohen B: An overview of the immune system. Lancet 357:1777-1789. 2001
22. Pizzo P A, Commers J, Cotton D, et al: Approaching the controversies in antibacterial management of cancer patients. Am J Med 76:436-449, 1984
23. Shiina T, Inoko H, Kulski J K: An update of the HLA genomic region, locus information and disease associations: 2004. Tissue Antigens 64:631-649, 2004
24. Sioud M: How does autoimmunity cause tumour regression? A potential mechanism involving cross-reaction through epitope mimicry. Mol Med 8:115-119, 2002
25. Vigouroux 5, Yvon F, Biagi F, et al: Antigen-induced regulatory T cells. Blood 104:26-33, 2004
26. von Mensdorff-Pouilly 5, Gourevitch M M, Kenemans P. et al: Humoral immune response to polymorphic epithelial mucin (MUC-1) in patients with benign and malignant breast tumours. Eur J Cancer 32A: 1325-1331, 1996

The invention claimed is:

1. A composition for treatment of a tumour in a patient, comprising
   (i) whole tumour cells that are allogeneic or xenogeneic to tumour cells in the patient;
   (ii) a lysate of a tumour cell that is syngeneic to tumour cells in the patient; and
   (iii) a pharmaceutically acceptable excipient.
2. The composition according to claim 1, further comprising a lysate of an allogeneic or xenogeneic cell of (i).
3. The composition according to claim 1, wherein the allogeneic or xenogeneic cells of (i) are brain-derived cells.
4. The composition according to claim 3, wherein the syngeneic cell of (ii) is a brain-derived cell.
5. The composition according to claim 1, wherein the allogeneic or xenogeneic cells of (i) are derived from the tumours of two or more heterozygous individuals.
6. A method for producing a medicament for treating a tumour of a patient wherein said method comprises combining (i) whole tumour cells that are allogeneic or xenogeneic to tumour cells in the patient and (ii) a lysate of a cell that is syngeneic to the tumour.
7. The method, according to claim 6, wherein the tumour of the patient is of the same histological grade as the tumour of the allogeneic or xenogeneic cells of (i).
8. The method, according to claim 6, wherein the allogeneic or xenogeneic tumour cells of (i) are derived from tumours of two or more heterozygous individuals.
9. A method for treatment of a tumour in a patient, comprising administering to a patient a composition comprising:
   (i) whole tumour cells that are allogeneic or xenogeneic to tumour cells in the patient;
   (ii) a lysate of a tumour cell that is syngeneic to tumour cells in the patient; and
   (iii) a pharmaceutically acceptable excipient.
10. The method, according to claim 9, wherein said composition further comprises a lysate of an allogeneic or xenogeneic cell of (i).
11. The method, according to claim 9, wherein the allogeneic or xenogeneic cells of (i) are brain-derived cells.
12. The method, according to claim 11, wherein the syngeneic cell of (ii) is a are brain-derived cell.
13. The method, according to claim 9, wherein the allogeneic or xenogeneic cells of (i) are derived from the tumours of two or more heterozygous individuals.

* * * * *